(12) United States Patent
Haselby

(10) Patent No.: US 9,192,497 B2
(45) Date of Patent: Nov. 24, 2015

(54) APPARATUS AND METHODS FOR IMPROVED STENT DEPLOYMENT

(75) Inventor: Kenneth Haselby, Battle Ground, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 690 days.

(21) Appl. No.: 13/062,429

(22) PCT Filed: Sep. 4, 2009

(86) PCT No.: PCT/US2009/004994
§ 371 (c)(1),
(2), (4) Date: Mar. 29, 2011

(87) PCT Pub. No.: WO2010/027485
PCT Pub. Date: Mar. 11, 2010

(65) Prior Publication Data
US 2011/0178588 A1     Jul. 21, 2011

Related U.S. Application Data

(60) Provisional application No. 61/094,506, filed on Sep. 5, 2008.

(51) Int. Cl.
*A61F 2/06*     (2013.01)
*A61F 2/966*     (2013.01)
(Continued)

(52) U.S. Cl.
CPC ............... *A61F 2/966* (2013.01); *A61F 2/915* (2013.01); *A61F 2/95* (2013.01);
(Continued)

(58) Field of Classification Search
CPC ......... A61F 2/2427–2/2439; A61F 2/95–2/97; A61F 2002/9505–2002/9665
USPC ............... 606/108, 191, 198; 623/1.11, 1.12, 623/1.13, 1.14, 1.23, 2.11
See application file for complete search history.

(56) References Cited

U.S. PATENT DOCUMENTS

| 5,480,423 A | 1/1996 | Ravenscroft et al. |
| 5,683,451 A | 11/1997 | Lenker et al. |
| (Continued) | | |

FOREIGN PATENT DOCUMENTS

| DE | 10 2006 053748 B3 | 4/2008 |
| JP | 2003-502107 | 1/2003 |
| (Continued) | | |

OTHER PUBLICATIONS

International Search Report and Written Opinion for PCT/US2009/004994 dated Dec. 10, 2009, 17 pgs.
(Continued)

*Primary Examiner* — Katherine Rodjom
*Assistant Examiner* — Jonathan Hollm
(74) *Attorney, Agent, or Firm* — Brinks Gilson & Lione

(57) ABSTRACT

Apparatus for facilitating deployment of a an implantable medical device includes a control member (20) having at least one tine member (35-37). A proximal region (35b-37b) of at least one of the tine members (35-37) is configured to engage an associated portion of a stent (60). In use, the control member (20) comprises a contracted delivery configuration in which the proximal region of the at least one of the tine member (35-37) is radially contracted, to radially constrain the associated portion of the stent (60). The control member (20) also comprises an expanded configuration in which the proximal region of the at least one of the tine member (35-37) expands radially outward relative to the central longitudinal axis to allow the stent to engage a body passage.

19 Claims, 6 Drawing Sheets

(51) Int. Cl.
*A61F 2/915* (2013.01)
*A61F 2/95* (2013.01)

(52) U.S. Cl.
CPC .............. *A61F 2002/91591* (2013.01); *A61F 2002/9511* (2013.01); *A61F 2002/9534* (2013.01); *A61F 2002/9665* (2013.01); *A61F 2220/0016* (2013.01); *A61F 2220/0058* (2013.01); *A61F 2220/0075* (2013.01); *A61F 2230/0013* (2013.01)

(56) References Cited

U.S. PATENT DOCUMENTS

| | | | |
|---|---|---|---|
| 5,902,263 | A | 5/1999 | Patterson et al. |
| 5,948,017 | A * | 9/1999 | Taheri ................. 623/1.14 |
| 6,398,802 | B1 | 6/2002 | Yee |
| 6,468,298 | B1 * | 10/2002 | Pelton ................. 623/1.11 |
| 6,653,525 | B2 * | 11/2003 | Ingenito et al. .......... 623/23.65 |
| 6,656,212 | B2 | 12/2003 | Ravenscroft et al. |
| 6,764,503 | B1 | 7/2004 | Ishimaru |
| 6,776,791 | B1 * | 8/2004 | Stallings et al. ........... 623/1.11 |
| 2001/0001833 | A1 | 5/2001 | Ravenscroft et al. |
| 2002/0151954 | A1 | 10/2002 | Brenneman |
| 2003/0135269 | A1 | 7/2003 | Swanstrom |
| 2004/0087965 | A1 | 5/2004 | Hebert et al. |
| 2004/0220653 | A1 | 11/2004 | Borg et al. |
| 2004/0220655 | A1 * | 11/2004 | Swanson et al. ........... 623/1.11 |
| 2005/0197694 | A1 | 9/2005 | Pai et al. |
| 2005/0288764 | A1 * | 12/2005 | Snow et al. ............ 623/1.11 |
| 2006/0020319 | A1 * | 1/2006 | Kim et al. ............ 623/1.11 |
| 2006/0041244 | A1 * | 2/2006 | Hohmann et al. .......... 604/509 |
| 2006/0069422 | A9 * | 3/2006 | Bolduc et al. ............ 623/1.11 |
| 2006/0095116 | A1 * | 5/2006 | Bolduc et al. ............ 623/1.16 |
| 2007/0088431 | A1 * | 4/2007 | Bourang et al. ........... 623/2.11 |
| 2007/0135826 | A1 | 6/2007 | Zaver et al. |
| 2008/0033528 | A1 * | 2/2008 | Satasiya et al. ........... 623/1.15 |
| 2008/0262592 | A1 * | 10/2008 | Jordan et al. ............ 623/1.11 |
| 2009/0030497 | A1 * | 1/2009 | Metcalf et al. ........... 623/1.12 |

FOREIGN PATENT DOCUMENTS

| | | |
|---|---|---|
| JP | 2003530916 | 10/2003 |
| JP | 2005-520627 | 7/2005 |
| WO | WO96/09013 | 3/1996 |
| WO | WO03/079935 | 10/2003 |
| WO | WO2006/005082 | 1/2006 |
| WO | WO2007/022496 | 2/2007 |
| WO | WO2007/092354 | 8/2007 |
| WO | WO2008/084252 | 7/2008 |

OTHER PUBLICATIONS

International Search Report and Written Opinion for PCT/US2009/004994 mailed Oct. 12, 2009, 17 pgs.
English Translation of Office Action for Japanese Patent Application No. 2011-526049 dated Sep. 25, 2013, 2 pgs.
Examination Report No. 1 for Australian Patent Application No. 2009288697 issued Feb. 28, 2013, 3 pgs.
International Preliminary Report on Patentability for PCT/US2009/004994 issued Mar. 17, 2011, 9 pgs.
Office Action for JP2011-526049 dated Jun. 17, 2014, 5 pgs including English translation.
Examination Report for EPO09789264.0 dated Aug. 14, 2015, 3 pgs.

* cited by examiner

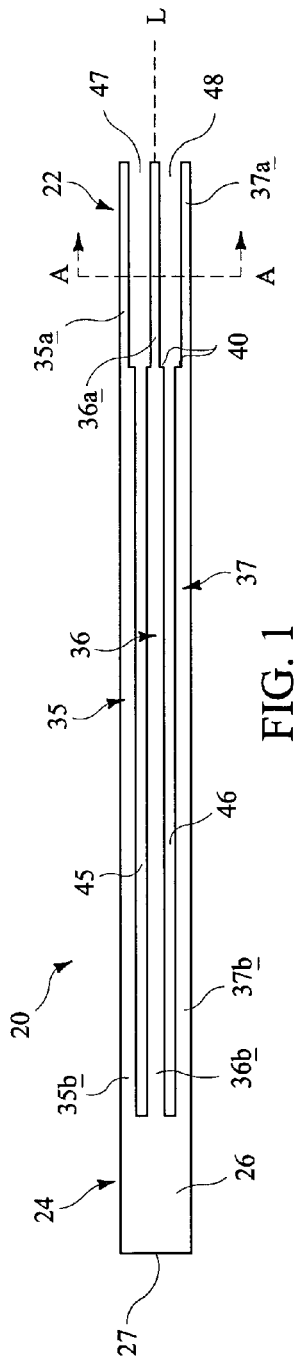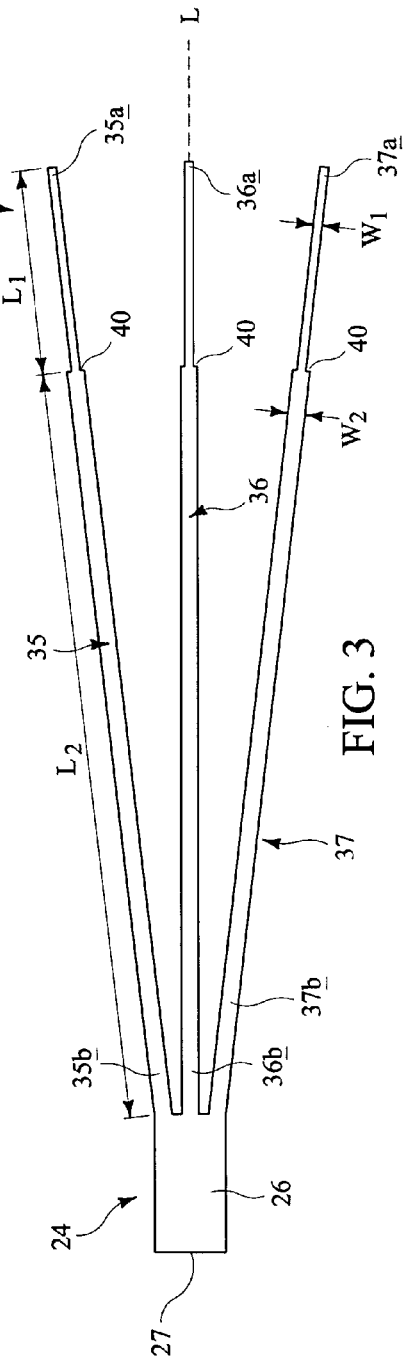

APPARATUS AND METHODS FOR IMPROVED STENT DEPLOYMENT

RELATED APPLICATIONS

The present patent document is a §371 filing based on PCT Application Serial No. PCT/US2009/004994, filed Sep. 4, 2009 (and published as WO 2010/027485 A1 on Mar. 11, 2010), designating the United States and published in English, which claims the benefit of the filing date under 35 U.S.C. §119(e) of Provisional U.S. Patent Application Ser. No. 61/094,506, filed Sep. 5, 2008. All of the foregoing applications are hereby incorporated by reference in their entirety.

TECHNICAL FIELD

The present invention relates generally to medical devices, and more particularly, to apparatus and methods for improved deployment of stents or other implantable medical devices.

BACKGROUND ART

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel is wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as Nitinol, the shape-memory alloy may be employed to cause the stent to return to a predetermined configuration upon removal of the sheath or other device maintaining the stent in its pre-deployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent formed of a series of substantially straight segments interconnected by a series of bent segments. The trigger wires may be disposed through, and pull upon, the bent segments to pull the stent closely against the delivery catheter. Trigger wires also may be used in conjunction with different stent designs, such as cannula-cut stents having acute or pointed bends. In the latter embodiment, the trigger wires may be looped around one or more vertices formed beneath the proximal and/or distal apices, for example a location where an individual apex splits into two separate strut segments.

If trigger wires are used to deploy stents, typically the actuation of the trigger wire causes full radial expansion of the stent, such that the stent engages an inner wall of a duct, vessel or the like. Barbs of the stent may engage the body passage, and the deployed stent may be difficult or impossible to recapture or reposition at this time. Further, upon release of the trigger wire, as the stent is expanding it may foreshorten or otherwise move an undesired amount with respect to the body passage. Therefore, the actuation of a conventional trigger wire may yield inaccurate positioning of a stent that engages a body passage and may be difficult to retrieve.

The problems are manifest not only in the deployment of stents but also in the deployment of stent grafts and other implantable medical devices.

DISCLOSURE OF THE INVENTION

The present invention seeks to provide an improved apparatus, introducer, for deploying a stent or other implantable medical device and an improved method of deploying an implantable medical device.

The present embodiments provide apparatus and methods for facilitating deployment of a stent or other medical device. In one embodiment, the apparatus comprises a control member having at least one tine member. A proximal region of at least one of the tine members is configured to engage an associated portion of a stent. The control member comprises a contracted delivery configuration in which the proximal region of the at least one of the tine member is radially contracted, relative to a central longitudinal axis of the control member, to radially constrain the associated portion of the stent. The control member also comprises an expanded configuration in which the proximal region of the at least one tine member expands radially outward relative to the central longitudinal axis to allow the stent to engage a body passage. The proximal region of the at least one tine member is selectively and incrementally movable between the contracted and expanded configurations to facilitate positioning of the stent.

The control member may be formed from a cannula having at least one slit formed therein, where the slit separates adjacent tine members. The cannula may comprise a shape memory alloy or other suitable material. Further, the proximal region of the at least one tine member may comprise a first width, and a distal region of the at least one tine member may comprise a second width. The first width preferably is less than the second width to form a stepped portion between the proximal and distal regions of the at least one tine member. The proximal region of the tine member may be sized to be advanced through a bore of the stent, while the distal region of the tine member comprises a width larger than the bore of the stent. Accordingly, the stepped portion may be configured to abut the stent to substantially inhibit distal movement of the stent with respect to the control member when the at least one tine member is coupled to the stent.

In one exemplary method of use, an outer cannula having a lumen is sized for longitudinal movement over a portion of the distal region of the at least one tine member. Selective proximal advancement of the outer cannula over the distal region of the at least one tine member incrementally urges the proximal region of the at least one tine member in a radially inward direction relative to the central longitudinal axis. Conversely, selective distal retraction of the outer cannula over the distal region of the at least one tine member permits incremental radial expansion of the proximal region of the at least one tine members relative to the central longitudinal axis. Accordingly, the amount of incremental expansion or contraction of the stent may be controlled in part by the selective incremental movement of the outer cannula with respect to the tine members.

Advantageously, the provision of a delivery system employing the apparatus and methods described herein may permit improved positioning of a stent, or stent-graft, inside of a body passage. The apparatus and methods also permit an amount of recapture of a stent prior to full deployment. Moreover, any undesirable foreshortening, which typically occurs when conventional trigger wires release a stent, may be reduced or eliminated by use of the control member and associated tine members.

The present invention may be used for the deployment of stents, stent grafts, vena cava filters and other implantable medical devices.

BRIEF DESCRIPTION OF THE DRAWINGS

Embodiments of the present invention are described below, by way of example only, with reference to the accompanying drawings, in which:

FIG. 1 is a side view of an exemplary control member in a contracted state;

FIG. 2 is a cross-sectional view along line A-A of FIG. 1;

FIG. 3 is a side view of the control member of FIG. 1 in a partially or fully expanded state;

DESCRIPTION OF THE PREFERRED EMBODIMENTS

Figure 4:
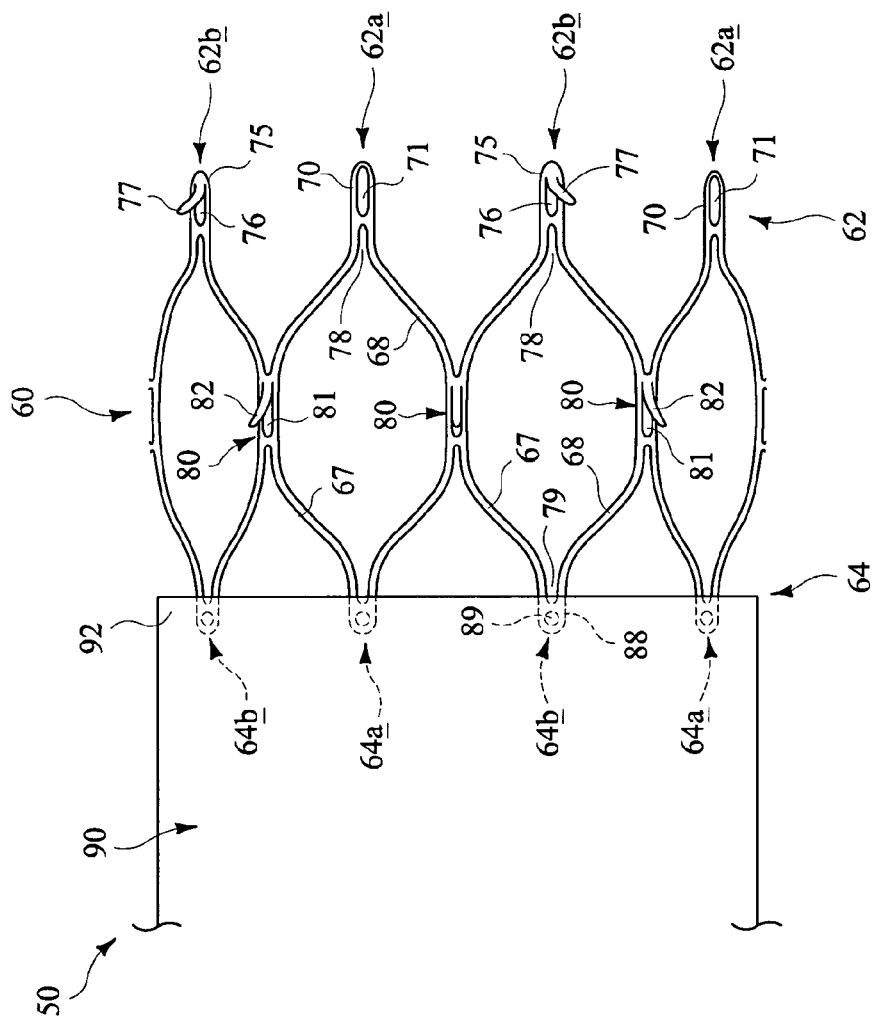
FIG. 4 is a side view depicting a proximal region of an exemplary stent-graft for used with the control member of FIGS. 1-3.

In the present application, the term "proximal" refers to a direction that is generally closest to the heart during a medical procedure, while the term "distal" refers to a direction that is furthest from the heart during a medical procedure.

The preferred embodiments taught below are described in connection with the deployment of a stent or stent graft. It is to be understood that the apparatus and method can be used for deploying of a range of implantable medical devices including stents, stent grafts, vena cava filters, occlusion devices and so on.

Referring to FIGS. 1-3, an apparatus for deploying a stent, or stent-graft, is disclosed. The apparatus comprises a control member 20 having proximal and distal regions 22 and 24. The control member 20 may be formed from a cannula 26 having a lumen 27 extending between the proximal and distal regions 22 and 24. As described further below, selective actuation of the control member 20 may permit at least partial radial expansion of a stent within a body passage, and also may permit at least partial radial contraction of the stent to permit repositioning of the stent within the body passage.

The cannula 26 of the control member 20 may comprise a shape-memory material such as a nickel-titanium alloy, or alternatively, stainless steel or another suitable material, as explained below. The proximal region 22 of the control member 20 comprises at least one tine member configured to engage a portion of a stent. The control member 20 may include a plurality of tine members. For example, as shown in FIGS. 1-3, the control member 20 comprises five tine members 35-39 disposed about the circumference of the control member 20, as best seen in FIG. 2, although only three tine members 35-37 are shown for clarity in the side views of FIG. 1 and FIG. 3. Any number of tine members may be employed, that is greater or fewer than five tine members.

The tine member 35-39 each comprise proximal and distal regions. As shown in FIG. 1, the tine member 35 comprises a proximal region 35a and a distal region 35b, while the tine member 36 comprises a proximal region 36a and a distal region 36b, and the tine member 37 comprises a proximal region 37a and a distal region 37b. The proximal regions of the tine members may form a tip that may be tapered or blunt.

The tine members 35-39 may be formed into the cannula 26 by forming one or more longitudinal slits in lateral surfaces of the cannula 26, for example using a laser or other suitable cutting technique, along the proximal region 22 of the control member 20. The tine members also may be attached to the cannula 26 by soldering, welding, or other methods. The provision of a proximal longitudinal slit 47 separates the proximal regions 35a and 36a of the adjacent tine members 35 and 36. Similarly, a proximal longitudinal slit 48 separates the proximal regions 36a and 37a of the adjacent tine members 36 and 37. Further, the provision of a distal longitudinal slit 45 formed into the cannula 26 separates the distal regions 35b and 36b of adjacent tine members 35 and 36, respectively, while the provision of a distal longitudinal slit 46 formed into the cannula 26 separates the distal regions 36b and 37b of adjacent tine members 36 and 37, respectively, as shown FIG. 1.

In one embodiment, a length of the proximal longitudinal slits 47 and 48 is less than a length of the distal longitudinal slits 45 and 46. Accordingly, the proximal regions of the tine members 35-39 comprise a length $L_1$, while the distal regions of the tine members 35-39 comprise a length $L_2$, whereby the length $L_1$ is less than the length $L_2$, as shown in FIG. 3. In one example, the length $L_2$ is about 2 to 8 times greater than the length $L_1$. Solely by way of example, the length $L_2$ may range from about 2 to 20 cm, while the length $L_1$ may range from about 0.5 to about 6 cm. The length $L_1$ preferably is sufficient to cause the proximal regions of one or more tine members 35-39 to engage a portion of a stent, for example by being disposed through a bore of the stent, as described in FIGS. 9-10 below. Further, the proximal longitudinal slits 47 and 48 preferably are circumferentially wider than the distal longitudinal slits 45 and 46. Accordingly, the proximal regions of the tine members 35-39 comprise a width $w_1$, while the distal regions of the tine members 35-39 comprise a width $w_2$, whereby the width $w_1$ is less than the width $w_2$, as shown in FIG. 3. Therefore, a stepped portion 40 is formed where the proximal regions 35a-37a transition into the wider distal regions 35b-37b, as shown in FIG. 1 and FIG. 3. The stepped portion 40 preferably is sized and configured to engage and/or abut a portion of a stent, for purposes explained further below.

The control member 20 has a contracted delivery configuration, shown in FIG. 1, and also has a partially or fully deployed expanded configuration, as shown in FIG. 3. In the contracted delivery configuration, the proximal regions of the tine members 35-39 are radially contracted, such that they preferably are substantially parallel to a central longitudinal axis L of the control member 20, as generally depicted in FIG. 1. In the partially or fully expanded configurations, the proximal region of at least one of the tine members 35-39 expands radially outward relative to the central longitudinal axis L, as depicted in FIG. 3.

As explained with regard to FIGS. 9-10 below, the tine members 35-39 are selectively movable in incremental amounts between the contracted and expanded configurations shown in FIGS. 1 and 3, respectively. In one exemplary method, described below, the proximal regions of the tine members 35-39 are selectively movable in incremental amounts in both radially inward and outward directions, to facilitate positioning of a stent within a body passage in a controlled manner.

Referring now to FIG. 4, an exemplary stent-graft 50, having a proximally-located stent 60 coupled to a graft material 90, may be deployed in a controlled manner using the control member 20 of FIGS. 1-3. The stent 60 may be manufactured from a continuous cylinder into which a pattern may be cut by a laser or by chemical etching to produce slits in the wall of the cylinder. The resulting structure may then be heat set to give it a desired final configuration. As shown in FIG. 4, the final configuration may include a shape having a series of proximal apices and a series of distal apices. A proximal end 62 of the stent 60 may comprise multiple adjacent proximal apices 62a and 62b, while a distal end 64 of the stent 20 may comprise multiple adjacent distal apices 64a and 64b, as shown in FIG. 4. The stent 60 may be provided in accordance with a self-expanding attachment stent, for example, described in co-pending U.S. application Ser. No. 12/364, 162, filed on Feb. 2, 2009, which is hereby incorporated by reference in its entirety.

In FIG. 4, at least one pair of adjacent, proximal apices 62a and 62b may comprise different features. For example, as shown in FIG. 4, a first proximal apex 62a may comprise an end region 70 having an aperture or bore 71 formed therein, wherein the bore 71 is configured to receive a proximal region of one of the tine members 35-39, as explained further below. A second, adjacent proximal apex 62b may comprise an end region 75 having an integral barb 77 formed therein, as shown in FIG. 4. The barb 77 may be formed by laser cutting a desired barb shape into the end regions 75. A slit 76 therefore is formed into each end region 75 after the desired barb shape is formed, as shown in FIG. 4. Once the desired barb shape is cut, a main body of the barb 77 may be bent in a radially outward direction with respect to the end region 75. The angle may comprise any acute angle, or alternatively may be substantially orthogonal or obtuse. If desired, the barb 77 may be sharpened, for example, by grinding the tip of the barb, to facilitate engagement at a target tissue site.

The apices 62a, 62b may be all the same or may differ from one another. In an embodiment, they may all include barbs 77. In another embodiment, there may not be provided any barbs 77 at the apices 62a, 62b themselves.

Referring still to FIG. 4, the stent 60 may comprise at least one strut segment disposed between the proximal and distal apices. For example, multiple angled strut segments may be disposed between a first proximal apex 62a and a corresponding distal apex 64a, and an identical set of angled strut segments may be disposed between an adjacent, second proximal apex 62b and a corresponding distal apex 64b. By way of example, a first proximal apex 62a extends distally and splits into first and second angled strut segments 67 and 68, respectively, thereby forming a proximal vertex 78, as shown in FIG. 4. In a compressed state, the first and second angled strut segments 67 and 68 may be compressed such that they are substantially parallel to one another. Similarly, each distal apex 64a and 64b may extend in a proximal direction and split into the first and second angled strut segments 67 and 68, respectively, thereby forming a distal vertex 79. A first angled strut segment 67 may meet with an adjacent second angled strut segment 68, thereby forming a transition region 80. In this manner, the stent 60 may be formed into a continuous, generally cylindrical shape, as shown in FIG. 4.

Expansion of the stent 60 is at least partly provided by the angled strut segments 67 and 68, which may be substantially parallel to one another in a compressed state, but may tend to bow outward away from one another in the expanded state shown in FIG. 4. The stent 60 may be formed from any suitable material, such as a laser-cut Nitinol cannula. If manufactured from Nitinol, the stent 60 may be inclined to assume the expanded state shown in FIG. 4 upon removal of a delivery sheath, such as the outer sheath 140 of FIG. 8 below.

Each transition region 80 may comprise a larger surface area relative to the angled segments, since the transition regions are composed substantially of multiple different angled segments 67 and 68. The stent 60 may comprise at least one barb 82 disposed in at least one of the transition regions 80. The barb 82 may be formed integrally, as part of the strut, or may comprise an external barb that is adhered to a surface of the transition regions 80. As shown in FIG. 4, multiple integral barbs 82 are provided. Like the barbs 77 noted above, the barbs 82 may be formed by laser cutting a desired barb shape into the transition regions 80. A slit 81 therefore is formed into the transition region 80 after the desired barb shape is formed, as shown in FIG. 4. Since the transition regions 80 may comprise an increased surface area relative to other regions of the stent 60, it may be easier to perforate portions of the transition regions 80 without adversely affecting the structural integrity of the stent. Once the desired barb shape is cut, a main body of the barb 82 may be bent in an outward direction at any angle with respect to the transition region 80 and optionally may be sharpened to facilitate engagement at a target tissue site.

Each of the distal apices 62a and 62b may comprise an end region 88 having a bore 89 formed therein, as shown in FIG. 4. The distal end 64 of the stent 80 may be coupled to a proximal end 92 of the graft material 90. The distal apices 62a and 62b may be coupled to the graft material, for example, using one or more sutures that are looped through the graft material and the bores 89 of the stent 80. In this manner, the stent 60 may be used as an attachment stent for endovascular graft fixation. For example, the graft material 90 may overlap with an aneurysm to seal off fluid flow into the aneurysm, while the proximal end 62 of the stent 60 may extend in a proximal direction away from the graft material, for example to engage a healthy portion of a vessel wall away from a diseased portion of the aneurysm. As will be apparent, one or more additional stents may be coupled to an inner or outer surface of the graft material 90, that is at a location distal to the stent 60, to help maintain patency throughout the graft material.

The stent 60 has a reduced diameter delivery configuration, or a compressed configuration, so that it may be advanced to a target location within a vessel or duct. The stent 60 also has an expanded deployed state to apply a radially outward force upon at least a portion of a vessel or duct, for example to maintain patency within a passageway or to hold open the lumen of a graft. In the expanded state, fluid flow is allowed through a central lumen of the stent 60. Further, the struts of the stent 60 may comprise a substantially flat wire profile or may comprise a rounded profile. As best seen in FIG. 4, the struts of the stent 60 generally comprise a flat wire profile.

The stent 60 may be manufactured from a super-elastic material. Solely by way of example, the super-elastic material may comprise a shape-memory alloy, such as a nickel titanium alloy (Nitinol). If the stent 60 comprises a self-expanding material such as Nitinol, the stent may be heat-set into the desired expanded state, whereby the stent 60 can assume a relaxed configuration in which it assumes the preconfigured first expanded inner diameter upon application of a certain cold or hot medium. Alternatively, the stent 60 may be made from other metals and alloys that allow the stent 60 to return to its original, expanded configuration upon deployment, without inducing a permanent strain on the material due to compression. Solely by way of example, the stent 60 may comprise other materials such as stainless steel, cobalt-chrome alloys, amorphous metals, tantalum, platinum, gold and titanium. The stent 60 also may be made from non-metallic materials, such as thermoplastics and other polymers.

While one exemplary stent 60 is shown in FIG. 4 and described in FIGS. 9-10 below, various alternative stent configurations may be used in conjunction with the control member 20 of FIGS. 1-3 and the other apparatus described further in FIGS. 5-10 below. Moreover, the stent may be deployed alone, or as part of a stent-graft system, as depicted herein, or as part of any other implantable medical device.

Figure 5:
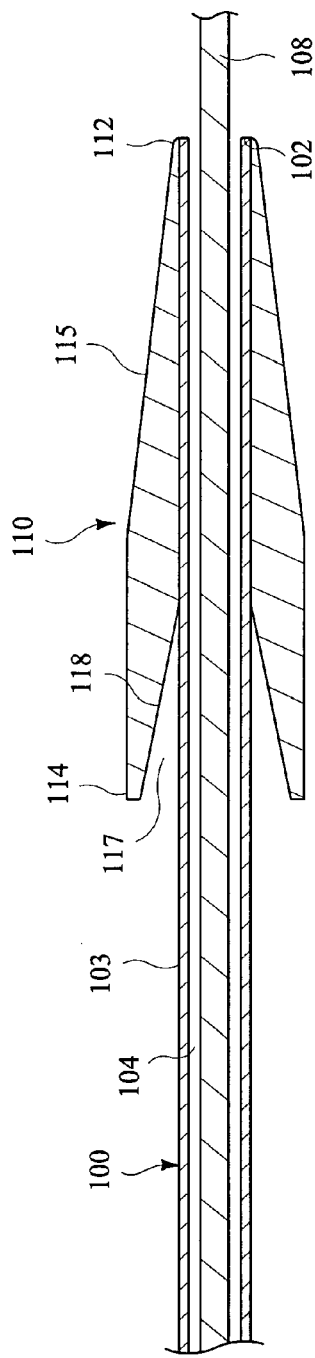
FIG. 5 is a side-sectional view of an inner cannula disposed over a wire guide.

Referring now to FIG. 5, a side-sectional view of an inner cannula 100 and an atraumatic tip 110, which may be used as part of a deployment device in conjunction with the control member 20, are shown. The inner cannula 100 comprises a tubular member having proximal and distal regions, and a lumen 104 extending between the proximal and distal regions. The lumen 104 of the inner cannula 100 is sized to allow the inner cannula 100 to be advanced over a wire guide 108, as depicted in FIG. 5.

The atraumatic tip 110 may be affixed to an exterior surface 103 along the distal region of the inner cannula 100, using a suitable adhesive or mechanical attachment mechanism, as depicted in FIG. 5. The atraumatic tip 110 may be formed from an atraumatic material, which comprises proximal and distal ends 112 and 114, respectively. The proximal end 112 comprises a smaller outer diameter relative to the distal end 114, with a taper 115 disposed therebetween. The proximal end 112 of the atraumatic tip 110 may be substantially flush with a proximal end 102 of the inner cannula 100, as depicted in FIG. 5. The atraumatic tip 110 further comprises a distal recess 117, which may be formed by providing a tapered inner surface 118 at the distal end 114 of the atraumatic tip 110, as shown in FIG. 5. As will be explained in further detail below, the distal recess 117 of the atraumatic tip 110 may receive a proximal portion of the control member 20 and the stent 60 during delivery of the stent 60 in the contracted delivery configuration.

Figure 6:
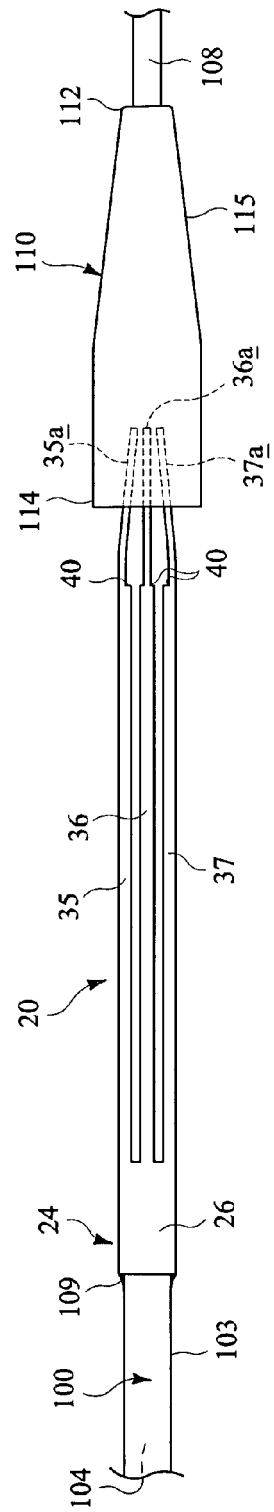
FIG. 6 is a side view of the control member of FIGS. 1-3 coupled to the inner cannula of FIG. 5.

Referring now to FIG. 6, the control member 20 of FIGS. 1-3 is coupled to the exterior surface 103 of the inner cannula 100. The distal region 24 of the control member 20 may be secured to the exterior surface 103 of the inner cannula 100 at an attachment region 109, for example using a solder, weld, or other suitable means. Preferably, the control member 20 is secured to the inner cannula 100 at a location such that a portion of the proximal regions 35a-37a of the tine members 35-37 may be disposed within the inner recess 117 of the atraumatic tip 110 when the tine members are in the contracted delivery configuration, as shown in FIG. 6. It should be noted that the tine members 35-39 are not rigidly secured to the inner cannula 100, but rather may expand in a radially outward direction, that is away from the inner cannula 100 and the atraumatic tip 110, in a deployed or partially deployed configuration.

Further, it should be noted that the inner cannula 100 extends proximally past the attachment region 109 and through the tine members 35-37. A portion of the inner cannula 100, which is disposed beneath the tine members 35-37, is not shown in FIG. 6 for illustrative purposes. However, the proximal end 102 of the inner cannula extends distal to the tine members 35-37 and may be affixed to the proximal end 112 of the atraumatic tip 110, as shown in FIG. 5.

Figure 7:
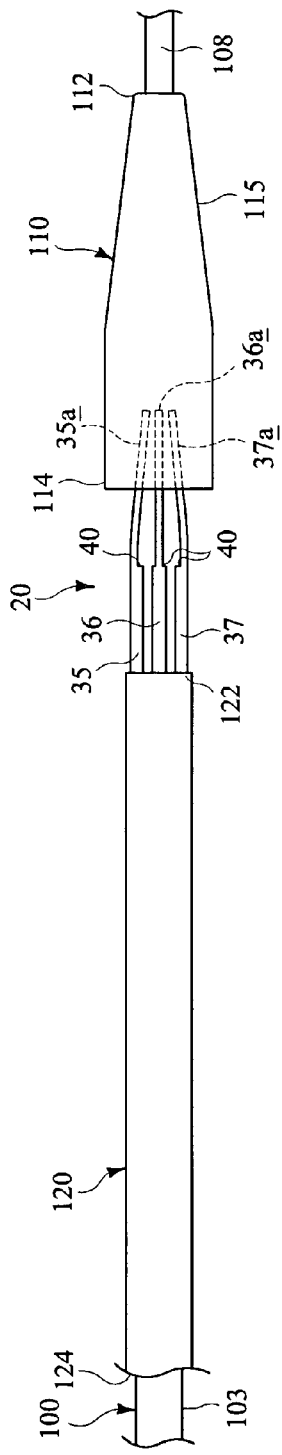
FIG. 7 is a side view showing an outer cannula disposed over a portion of the apparatus of FIG. 6.

Referring now to FIG. 7, a side view illustration depicts an outer cannula 120 disposed over the apparatus of FIG. 6. The outer cannula 120 comprises proximal and distal regions and a lumen 124 extending therebetween. The lumen 124 comprises an inner diameter that is larger than an outer diameter of the inner cannula 100, thereby permitting movement of the outer cannula 120 over the inner cannula 100. As will be set forth in FIGS. 9-10 below, longitudinal movement of outer cannula 120 with respect to the inner cannula 100 permits selective expansion and retraction of the tine members 35-39 of the control member 20, thereby facilitating controlled expansion, and if necessary contraction, of the stent 60.

Figure 8:
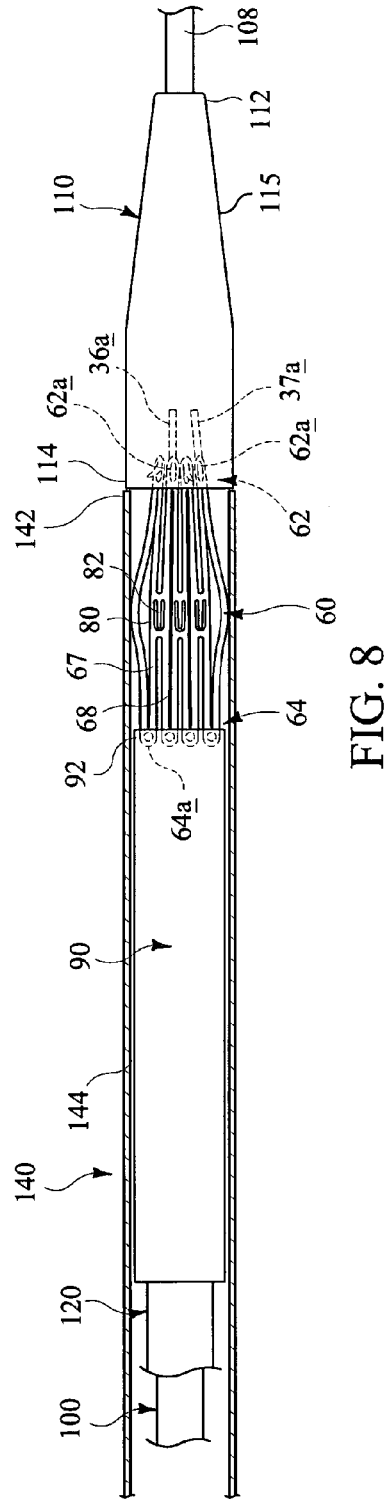
FIG. 8 is generally a side view illustrating the stent-graft of FIG. 4 used with the apparatus of FIGS. 5-7. An outer sheath is shown in a side-sectional format for illustrative purposes.

Referring to FIG. 8, the stent-graft 50 of FIG. 4 is coupled to the control member 20 in the contracted delivery configuration. In this state, the graft 90 of the stent-graft 50 may be placed over the outer cannula 120. At least a portion of the proximal end 62 of the stent 60 is coupled to the control member 20. Preferably, each of the alternating proximal apices 62a of the stent 60 is coupled to one of the tine members 35-39, as best seen in FIGS. 9-10 below. More specifically, the proximal region 35a of the tine member 35 may be looped through the bore 71 formed in one of the proximal apices 62a of the stent 60, as depicted in FIGS. 9-10. At this time, the stepped portion 40 of the tine member 35 may abut the proximal vertex 78 of the stent 60.

The remaining tine members 36-39 may be coupled to the other proximal apices 62a of the stent 60 in a similar manner. The stepped portions 40 on each of the tine members 35-39 may engage and/or abut the stent 60 and substantially inhibit distal movement of the stent 60. In this manner, the stent 60 may remain securely coupled to the control member 20. It should be noted that the tine members 35-39 are not disposed through the alternating proximal apices 62b, which comprise the barbs 77. Further, it should be noted that during delivery, when the stent 60 is coupled to the tine members 35-39 of the control member 20 as noted above, a proximal portion of the tine members 35-39 and a proximal portion of the stent 60 may extend into the inner recess 117 at the distal end 114 of the atraumatic tip 110, as depicted in FIG. 8.

Preferably, an outer sheath 140 is used to retain the stent-graft 50 in the contracted delivery configuration shown in FIG. 8. The outer sheath 140 has proximal and distal regions and a lumen 144 extending therebetween. A proximal end 142 of the outer sheath 140 extends over the stent 60 of the stent-graft 50, and may abut the distal end 114 of the atraumatic tip 110, as depicted in FIG. 8. With the entire assembly provided as shown in FIG. 8, the stent-graft 50 may be advanced towards a target site within a patient's vessel or duct over the wire guide 108.

Figure 9:
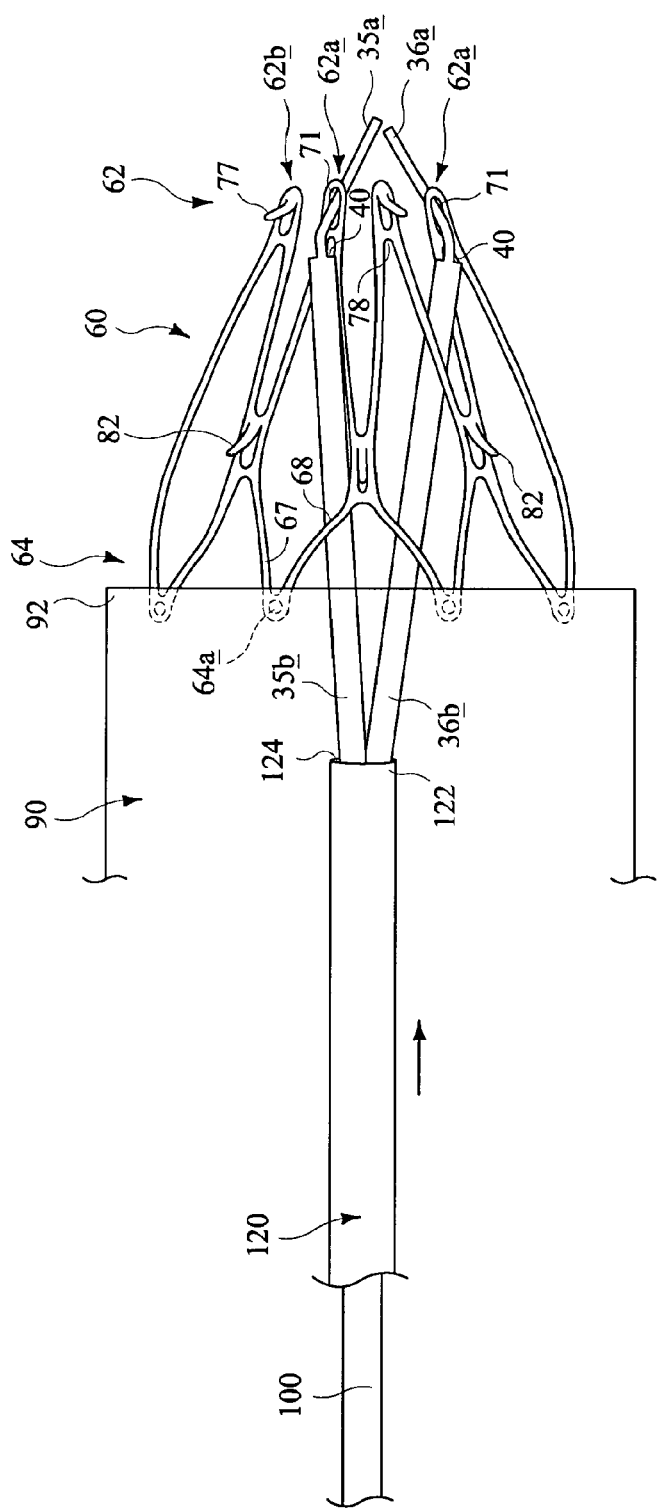
FIGS. 9-10 are side views illustrating an exemplary sequence of controlled deployment of the stent-graft of FIG. 4.
Figure 10:
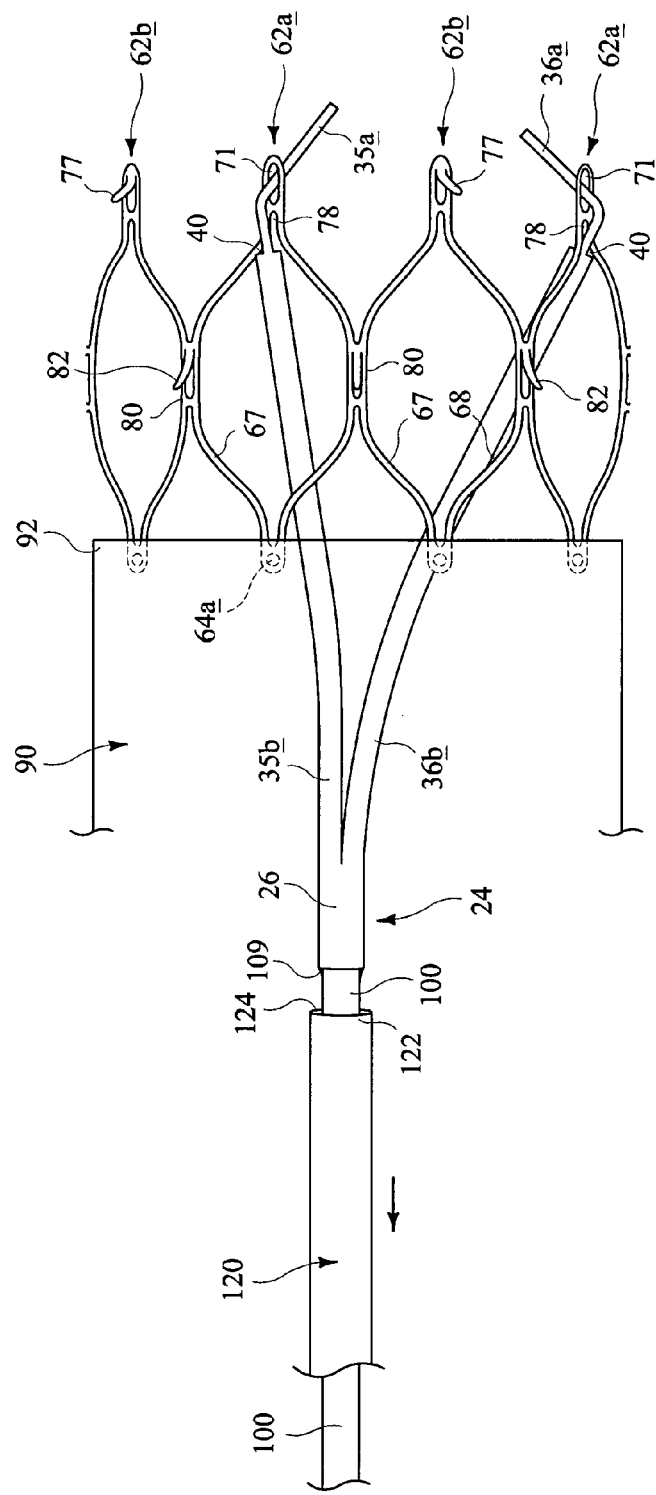

Referring now to FIGS. 9-10, prior to complete deployment of the stent-graft 50 into engagement with an inner wall of a body passage, a physician may incrementally deploy the stent 60, and also may incrementally contract the stent 60 as needed, thereby facilitating improved deployment and positioning of the stent 60. In a first step, with the apparatus delivered over the wire guide 108 as shown in FIG. 8, the stent 60 is generally aligned with a region of the body passage where it is desired to deploy the stent 60. This may be performed under fluoroscopic guidance or other suitable imaging techniques. Preferably, one or more radiopaque markers are provided on the stent 60 to facilitate alignment within the body passage.

Upon initial alignment of the stent 60, the outer sheath 140 of FIG. 8 may be distally retracted to expose the stent-graft 50. At this time, the stent 60 may partially self-expand, as depicted in FIG. 9, such that the proximal end 62 of the stent 60 may no longer engage the inner recess 117 at the distal end 114 of the atraumatic tip 110. As the proximal end 62 of the stent 60 self-expands, the stent is segments begin to urge each of the tine members 35-39 in a radially outward direction, as depicted in FIG. 9.

However, the longitudinal positioning of the outer cannula 120 may be used to limit the maximum radial expansion of the tine members 35-39, which in turn may limit the maximum radial expansion of at least the proximal end 62 of the stent 60. More specifically, when the outer cannula 120 is in a relatively proximal longitudinal position, as shown in FIG. 9, the outer cannula 120 may impose a relatively stiff restraining force upon the distal regions 35b and 356b of the tine members, which may prevent the proximal regions 35a and 36a of the tine members from further radially expanding. At this time, the stent 60 cannot further radially expand. Moreover, the stent 60 cannot slide backwards, i.e., distally, because the vertices 78, angled strut segments 67 and 68, or other strut portions will engage the stepped portion 40 of the tine members 35-39 of the control member 20.

Accordingly, when the outer sheath 140 is in a relatively proximal longitudinal position, and the outer cannula 120 imposes a relatively stiff restraining force upon the tine members 35-39, neither the barbs 77 nor the barbs 82 engage the inner wall of the body passage. This allows a physician to reposition the location of the stent 60 within the body passage, if desired.

Referring to FIG. 10, in a next step, the outer cannula 120 may be distally retracted with respect to the inner cannula 100. When in a relatively distal longitudinal position, the outer cannula 120 may expose a greater portion of the tine members 35-39, and also may expose the cannula 26 and attachment region 109 between the control member 20 and the inner cannula 100. Since the tine members 35-39 are no longer substantially constrained, the tine members 35-39 may have greater flexibility, and the radial force provided by the desired self-expansion of the stent 60 may urge the tine members 35-39 further radially to outward, as shown in FIG. 10.

In this manner, by moving the outer cannula 120 an incremental amount with respect to the inner cannula 100, the outer cannula 120 may permit movement of the tine members 35-39 an incremental amount between the contracted and expanded configurations, both in radially inward and outward directions, to facilitate positioning of the stent within the body passage. For example, as stent 60 radially expands in a controlled manner due to incremental distal retraction of the outer cannula 120, and the barbs 77 and 82 are about to engage the inner wall of the body passage, a physician may wish to advance the outer cannula 120 proximally with respect to the inner cannula 100 to recapture or retract the stent 60. Accordingly, any number of repositioning attempts may be made before final deployment of the stent 60.

Upon final positioning, the outer cannula 120 may be retracted distally a sufficient amount that causes the barbs 77 and 82 to fully engage the inner wall of the body passage. The inner cannula 100 then may be distally retracted to pull the proximal regions 35a and 36a of the tine members 35 and 36, as well as the other tine members, through their associated bores 71 in the stent. The tine members 35-39 then may be retracted distally into the confines of the outer cannula 120, and the inner and outer cannulae 100 and 120 may be removed from the patient's body.

Advantageously, the provision of a delivery system employing a control member 20, as described above, may permit improved positioning of the stent-graft 50 inside of a body, and also permits an amount of recapture of the stent 60 prior to full deployment. Moreover, any undesirable foreshortening, which typically occurs when conventional trigger wires release a stent, may be reduced or eliminated by use of the control member 20 and associated tine members.

It is preferred that there is provided a tine member for each stent apex 62a, 62b but in some embodiments only some of the apices of the stent may have associated tine members, in which case the stent 60 would contract y the contracting force over the entire stent produced by those parts of the stent which are coupled to the tines 35-37.

While various embodiments of the invention have been described, the to teachings herein are not limited thereto and must be construed having regard to the appended claims. Moreover, the advantages described herein are not necessarily the only advantages of the teachings herein and it is not necessarily expected that every embodiment of the invention will achieve all of the advantages described.

The disclosures in U.S. patent application No. 61/094,506, from which this application claims priority, and the abstract accompanying this Application are incorporated herein by reference.

The invention claimed is:

1. An apparatus for deploying a stent, the apparatus comprising:
a control member having at least one tine member comprising proximal and distal regions, where the proximal region of the at least one tine member is configured to engage an associated portion of a stent,
a sheath at least partially disposed over the at least one tine member in a constrained state,
where the control member comprises a contracted delivery configuration in which the proximal region of the at least one tine member is radially contracted and an expanded configuration in which the proximal region of the at least one of the tine member is radially expanded relative to a central longitudinal axis,
where the proximal region of the at least one tine member is selectively and incrementally movable between the contracted and expanded configurations to facilitate positioning of the stent within a body passage,
where the proximal region of the at least one tine member has a bend towards the central longitudinal axis in a state unconstrained by the sheath,
where the proximal region of the at least one tine member comprises a first width and a first length, and the distal region of the at least one tine member comprises a second width greater than the first width and a second length greater than the first length, such that a stepped portion is formed between the proximal and distal regions of the at least one tine member.

2. The apparatus of claim 1 further comprising an outer cannula having a lumen, where the outer cannula is sized for longitudinal movement over a portion of the distal region of the at least one tine member, where selective proximal advancement of the outer cannula over the distal region of the at least one tine member is configured to incrementally urge the proximal region of the at least one tine member in a radially inward direction relative to the central longitudinal axis.

3. The apparatus of claim 2 where selective distal retraction of the outer cannula over the distal region of the at least one tine member is configured to permit incremental radial expansion of the proximal region of the at least one tine members relative to the central longitudinal axis.

4. The apparatus of claim 2 further comprising:
an inner cannula having proximal and distal ends, where the inner cannula comprises a lumen disposed between the proximal and distal ends to permit advancement of the inner cannula over a wire guide,
where a distal region of the control member is affixed to an outer surface of the inner cannula, and
where the outer cannula is sized for longitudinal advancement over the inner cannula.

5. The apparatus of claim 4, further comprising an atraumatic tip disposed on the proximal end of the inner cannula, where the atraumatic tip comprises a distal end having an inner recess, and where the proximal region of the at least one tine member is disposed within the inner recess during delivery of the stent into the body passage.

6. The apparatus of claim 1 where the control member comprises:
a plurality of tine members; and
a cannula having at least one slit formed into the cannula, where the at least one slit is disposed between adjacent tine members.

7. The apparatus of claim 6 where the cannula comprises a shape memory alloy.

8. The apparatus of claim 1 where the proximal region of the at least one tine member is sized to be advanced through an associated portion of a stent.

9. A method for deploying a stent, the method comprising:
providing a control member having at least one tine member comprising proximal and distal regions;
providing a sheath at least partially disposed over the at least one tine member in a constrained state;
coupling the proximal region of the at least one tine member to an associated portion of a stent without an external wire;
advancing the control member into a body passage in a contracted delivery configuration in which the proximal region of the at least one tine member is radially contracted relative to a central longitudinal axis of the control member to radially constrain the associated portion of the stent;
deploying the control member to an expanded configuration in which the proximal region of the at least one tine member expands radially outward relative to the central longitudinal axis to allow the stent to expand, and further where the proximal region of the at least one tine member has a bend towards the central longitudinal axis in a state unconstrained by the sheath; and
selectively and incrementally moving the proximal region of the at least one tine member between the contracted and expanded configurations to facilitate positioning of the stent,
wherein the proximal region of the at least one tine member comprises a first width and a first length, and the distal region of the at least one tine member comprises a second width greater than the first width and a second length greater than the first length, such that a stepped portion is formed between the proximal and distal regions of the at least one tine member.

10. The method of claim 9 further comprising:
contracting the at least one tine member;
repositioning the stent; and
allowing the at least one tine member to expand to permit expansion of the stent.

11. The method of claim 10 further comprising proximally advancing an outer cannula over the distal region of the at least one tine member to incrementally urge the proximal region of the at least one tine member in a radially inward direction relative to the central longitudinal axis.

12. The method of claim 11 further comprising incrementally distally retracting the outer cannula over the distal region of the at least one tine member to permit incremental radial expansion of the proximal region of the at least one tine members relative to the central longitudinal axis.

13. The method of claim 10 where the proximal region of the at least one tine member comprises a first width, and the distal region of the at least one tine member comprises a second width, where the first width is less than the second width to form a stepped portion between the proximal and distal regions of the at least one tine member, the method further comprising:
advancing the proximal region of the tine member through a bore of the stent; and
abutting the stepped portion against the stent to substantially inhibit distal movement of the stent with respect to the control member when the at least one tine member is coupled to the stent.

14. An apparatus for deploying a stent, the apparatus comprising:
a control member having at least one tine member comprising proximal and distal regions, where the proximal region of the at least one tine member is configured to engage an associated portion of a stent,
where the control member comprises a contracted delivery configuration in which the proximal region of the at least one tine member is radially contracted and an expanded configuration in which the proximal region of the at least one of the tine member is radially expanded relative to a central longitudinal axis,
where the proximal region of the at least one tine member is selectively and incrementally movable between the contracted and expanded configurations to facilitate positioning of the stent within a body passage,
where the proximal region of the at least one tine member comprises a first width, and the distal region of the at least one tine member comprises a second width greater than the first width, such that a stepped portion is formed between the proximal and distal regions of the at least one tine member,
where the proximal region of the at least one tine member has a bend towards the central longitudinal axis, and
wherein the bend is disposed in the proximal region of the first width.

15. The apparatus of claim 14 further comprising an outer cannula having a lumen, where the outer cannula is sized for longitudinal movement over a portion of the distal region of the at least one tine member, where selective proximal advancement of the outer cannula over the distal region of the at least one tine member is configured to incrementally urge the proximal region of the at least one tine member in a radially inward direction relative to the central longitudinal axis.

16. The apparatus of claim 15 where selective distal retraction of the outer cannula over the distal region of the at least one tine member is configured to permit incremental radial expansion of the proximal region of the at least one tine members relative to the central longitudinal axis.

17. The apparatus of claim 15 further comprising:
an inner cannula having proximal and distal ends, where the inner cannula comprises a lumen disposed between the proximal and distal ends to permit advancement of the inner cannula over a wire guide,
where a distal region of the control member is affixed to an outer surface of the inner cannula, and where the outer cannula is sized for longitudinal advancement over the inner cannula.

18. The apparatus of claim 17, further comprising an atraumatic tip disposed on the proximal end of the inner cannula, where the atraumatic tip comprises a distal end having an inner recess, and where the proximal region of the at least one tine member is disposed within the inner recess during delivery of the stent into the body passage.

19. The apparatus of claim 14 where the control member comprises:
 a plurality of tine members; and
 a cannula having at least one slit formed into the cannula, where the at least one slit is disposed between adjacent tine members.

\* \* \* \* \*